United States Patent [19]

Sato et al.

[11] Patent Number: 4,962,763
[45] Date of Patent: Oct. 16, 1990

[54] MAGNETIC RESONANCE IMAGE SYNTHESIZING SYSTEM

[75] Inventors: Shinichi Sato, Yokohama; Koichi Sano, Sagamihara; Tetsuo Yokoyama, Tokyo; Hideki Koizumi, Katsuta, all of Japan

[73] Assignee: Hitachi, Ltd., Tokyo, Japan

[21] Appl. No.: 209,938

[22] Filed: Jun. 22, 1988

[30] Foreign Application Priority Data

Jun. 22, 1987 [JP] Japan .................. 62-153290

[51] Int. Cl.$^5$ .............................. A61B 5/055
[52] U.S. Cl. ................. 128/653 A; 128/653 AF; 324/306; 324/309; 324/312
[58] Field of Search ............ 128/653, 653 A, 653 AF; 324/306, 309, 312

[56] References Cited

U.S. PATENT DOCUMENTS

| | | | |
|---|---|---|---|
| 4,599,565 | 7/1986 | Hoenninger et al. | 324/309 |
| 4,607,222 | 8/1986 | Yokoyama et al. | 324/309 |
| 4,634,979 | 1/1987 | Riederer et al. | 324/312 |
| 4,728,893 | 3/1988 | Feinberg | 324/312 |
| 4,770,182 | 9/1988 | Damadian et al. | 128/653 |
| 4,786,872 | 11/1988 | Hoshino | 324/312 |
| 4,853,636 | 8/1989 | Yamamoto et al. | 324/309 |

OTHER PUBLICATIONS

Naruse et al, "Clinical Evaluation of Synthetic MR Images in Intracranial Diseases", SMRM, 1986, vol. 3, pp. 762-763.

*Primary Examiner*—Ruth S. Smith
*Attorney, Agent, or Firm*—Antonelli, Terry, Stout & Kraus

[57] ABSTRACT

A magnetic resonance image synthesizing system comprising a magnetic field generating section for generating a static magnetic field, a gradient magnetic field and a radio-frequency magnetic field and for irradiating those magnetic fields to an object to be examined, a receiver for detecting a magnetic resonance signal supplied from the object to be examined, a processing unit for calculating and constructing an MR image and distribution of blood velocity or relaxation time on the basis of the detected nuclear magnetic resonance signal, a sequence control section for controlling the gradient magnetic field and the radio-frequency magnetic field as well as the receiver, a display unit for displaying an MR image, and a manipulation section for specifying a necessary position on the screen of the display unit, the processing unit further making the display unit display an MR image calculated and synthesized on the basis of scanning parameters and a blood velocity or relaxation time defined in accordance with a position specified in the manipulation section.

4 Claims, 8 Drawing Sheets

MAGNETIC RESONANCE IMAGE SYNTHESIZING SYSTEM

BACKGROUND OF THE INVENTION

The present invention relates to a magnetic resonance image synthesizing system, and in particular to a magnetic resonance synthesizing system capable of displaying an arbitrary region of interest clearly.

Blood vessel imaging methods using magnetic resonance images (hereafter abbreviated to MR images) have been proposed as described in "Method for MR Angiography", Society of Magnetic Resonance in Medicine, VOL. 1 (1985), pp. 591 to 592, for example. In one method, images are obtained by using a pulse sequence for extracting signals from a moving region of a human body. In another technique, MR images in an expansion interval of a heart and MR images in a contraction interval of the heart are derived and a differential image is produced from the difference between those images. These methods are capable of displaying only moving portions. When flow velocities are different at respective portions in a case such as blood flow, for example, however, it is difficult to obtain clear images of a region of blood vessel of interest.

On the other hand, relaxation time enhanced images which are displayed with the difference between relaxation time values enhanced provide information which is important for clinical determination with respect to an affected part. In many cases, therefore, the images with enhanced relaxation time provide more important significance than spin density images representing morphological information. These images with relaxation time enhanced are obtained with different contrasts by changing scanning parameters such as the duration of irradiation of an RF pulse in the pulse sequence and the interval of its irradiation. For obtaining a desired image, therefore, it is necessary to obtain several images while changing scanning parameters, resulting in a problem of extremely long scanning time. Therefore, there has been proposed a scheme in which an image under an arbitrary scanning condition is synthesized on the basis of information of a plurality of images with relaxation time enhanced which were scanned beforehand.

In a method described in "Clinical Evaluation of Synthetic MR Images in Intracranial Diseases", SMRM '86, VOL. 3, pp. 762 to 763 (1986), for example, the spin density, the spin-lattice relaxation time and the spin-spin relaxation time are calculated from a plurality of images with relaxation time enhanced which were scanned beforehand. The calculated values are substituted into a signal strength calculating expression to calculate images with relaxation time enhanced at the time when the scanning parameters are arbitrarily changed.

Further, there also has been proposed a scheme in which an arbitrary synthetic image is directly calculated by computation of a plurality of images with relaxation time enhanced which were scanned beforehand.

Especially when an image representing only blood vessels is synthesized by using the former prior art, the phase rotation angle of the spin changes depending upon the blood velocity. Accordingly, the relationship between the phase angle of the resultant measured signal and the blood velocity is fixed in accordance with the scanning sequence. Even if there is a region of interest, therefore, the velocity of that region is unknown and hence a problem that the region is not necessarily displayed clearly.

Further, in the latter prior art, the scheme for calculating images with relaxation time enhanced is considered for a case where an image with relaxation time enhanced is to be synthesized. However, a synthesis and display scheme with due regard to man-machine interface is not shown.

SUMMARY OF THE INVENTION

An object of the present invention is to provide a magnetic resonance image synthesizing system in which by only setting necessary scanning conditions on a display screen on the basis of information supplied from on to several MR images without scanning a large number of MR images, an MR image corresponding to the scanning conditions thus set is automatically computed and synthesized to be displayed on a screen.

A magnetic resonance image synthesizing system according to the present invention comprises means for generating a static magnetic field, a gradient magnetic field and a radio-frequency magnetic field, means for irradiating those magnetic fields to an object to be examined, means for detecting a nuclear magnetic resonance signal supplied from the object to be examined, means for performing computation to reconstruct an image in accordance with nuclide density information based upon the detected nuclear magnetic resonance signal, means for displaying the reconstructed image, a sequence control section for controlling the gradient magnetic field, the high frequency magnetic field and the detecting means, and specifying means for specifying a position on a screen of the displaying means, upon indication of a scanning condition by the specifying means MR images being synthesized by the computing means computing pixel values in accordance with the scanning condition and displayed on the screen of the display means.

In accordance with one aspect of the present invention, the sequence control section has a sequence for measuring the blood velocity of the object to be examined, and the computing means derives distribution of blood velocity on the basis of a signal measured in accordance with the blood velocity measuring sequence, the distribution of blood velocity being stored in a memory section. Upon specifying a region of interest with respect to the blood flow in the specifying means, the computing means reads out the blood velocity of the region of interest from the memory section and computes scanning parameters which generates a clear image for the blood velocity. On the basis of the scanning parameters thus computed, an MR image is synthesized and displayed by the displaying means.

In accordance with another aspect of the present invention, the specifying means comprises a cursor for specifying a position on the screen of the display means, and the display means has a one-dimensional or two-dimensional display region indicated by the cursor. When an arbitrary position within the display region is indicated by the cursor to specify necessary parameters or a region of interest, the computing means calculates and synthesizes an MR image in accordance with the specified indication condition, and the synthesized MR image is displayed by the display means.

DESCRIPTION OF THE PREFERRED EMBODIMENTS

Embodiments of the present invention will now be described by referring to drawings.

Figure 1:
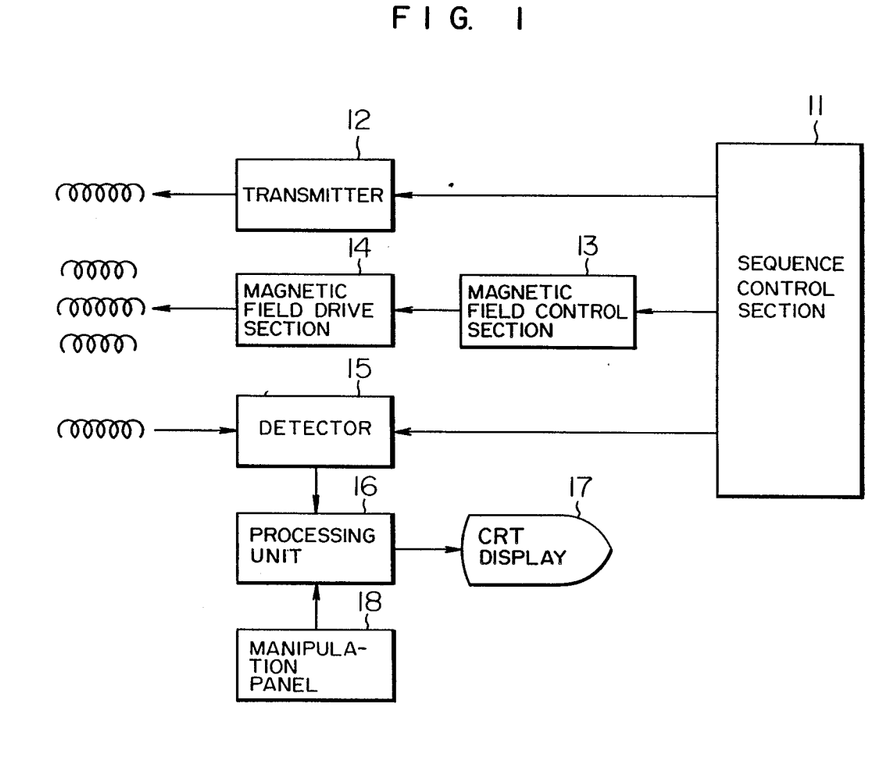
FIG. 1 is a block diagram showing an embodiment of a magnetic resonance image synthesizing system according to the present invention.

FIG. 1 shows an embodiment of entire configuration of a magnetic resonance image synthesizing system according to the present invention. In FIG. 1, a magnetic resonance image synthesizing system according to the present invention includes a sequence control section 11, a transmitter 12, a magnetic field control section 13, a magnetic field drive section 14, a detector 15, a processing unit 16, a CRT display 17 and a manipulation panel 18.

The transmitter 12 generates a radio-frequency pulse to make a specific nuclide of the object to be examined resonate. In accordance with a control signal outputted by the magnetic field drive section 13, the magnetic field drive section 14 generates a static magnetic field defining the resonance frequency of the MR signal and a gradient magnetic field which can be arbitrarily controlled in strength and direction. The detector 15 detects the MR signal generated by the object to be examined and then performs measurement. By controlling these, the sequence control section 11 controls various pulses generated to detect the MR signal supplied from the object to be examined and controls the magnetic fields.

On the basis of the measured signal taken in from the detector 15 the processing unit 16 performs reconstruction of an image or synthesis of a blood vessel image. The finally resultant image is displayed on the CRT display 17. The manipulation panel 18 is an input unit through which the operator inputs desired scanning conditions.

First of all, synthesis of a blood vessel image which is the first embodiment of the present invention will now be described.

When a blood vessel image is to be synthesized, MR images are derived beforehand by using a scanning sequence controlled by the sequence control section 11 and distribution of blood velocities at respective points on the screen is measured beforehand. A region of interest is then specified, and an MR image is constructed so that the blood velocity of the region corresponds to the highest intensity of the image. On the basis of relationship between the blood velocity at tat region and the phase of the NMR signal, a sequence of scanning parameters are set. By that sequence, an MR image is synthesized and displayed on the basis of MR images scanned already and the distribution of blood velocities.

Figure 2:
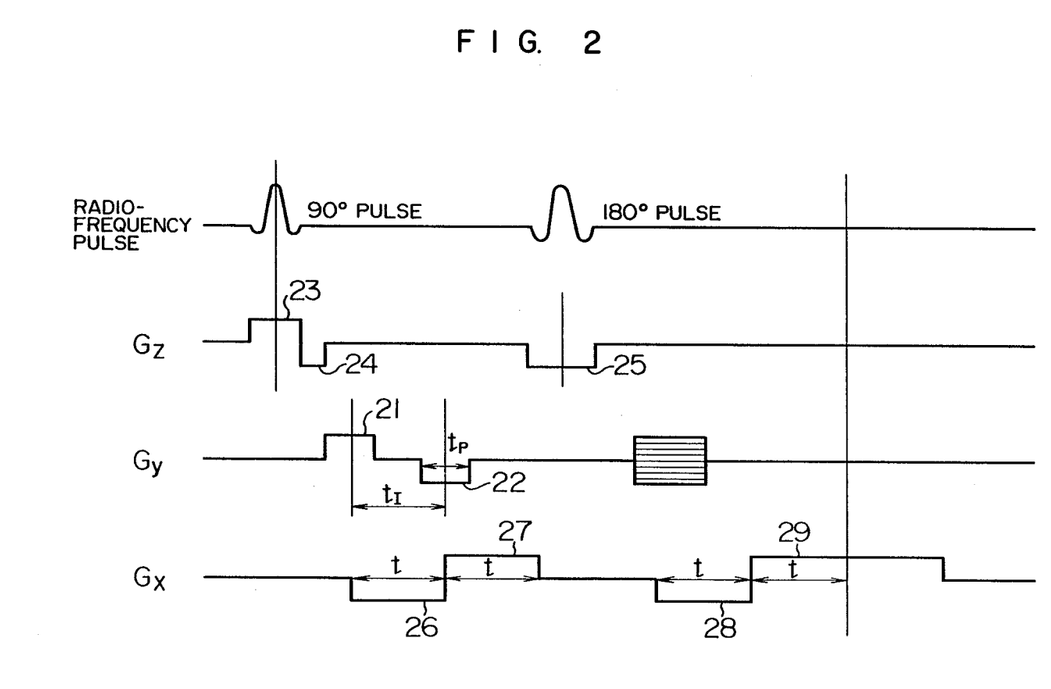
FIG. 2 shows an example of a pulse sequence for measuring the hydrogen atom density and the blood velocity of each region in the first embodiment of the present invention.
Figure 4:
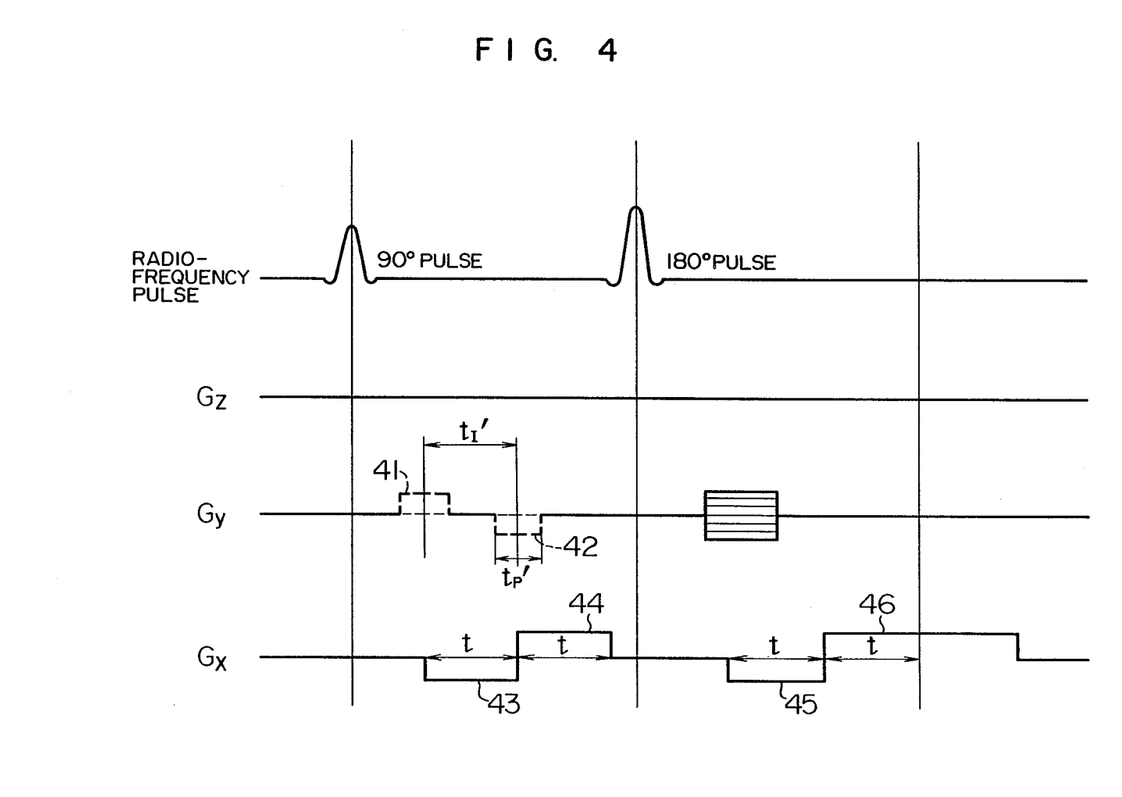
FIG. 4 shows an example of a pulse sequence for scanning a blood vessel image in the first embodiment of the present invention.

FIG. 2 shows an example of a pulse sequence for measuring beforehand hydrogen atom density and blood velocities at respective regions in the first embodiment of the present invention. FIG. 4 shows an example of a pulse sequence for scanning blood vessel images in the first embodiment of the present invention.

This sequence for measuring blood velocities is known and is described in detail in U.S. Application Ser. No. 133,069 filed Dec. 15, 1987 entitled "Nuclear Magnetic Resonance Imaging Method and Apparatus" by Sano et al now U.S. Pat. No. 4,870,362 and U.S. Application Ser. No. 881,405 filed July 2, 1986 entitled "NMR Imaging Method", a continuation application issuing as U.S. Pat. No. 4,844,077. Therefore, the principle of the measurement of blood velocities will not be described herein in detail.

When an NMR signal at a region where a blood flow exists is measured under the control of a fixed pulse sequence, the phase rotation angle θ of the measured signal is related to the blood velocity v at that region as:

$$\theta = 0.36 \gamma \cdot G \cdot t_p \cdot t_f \cdot V \tag{1}$$

where
$\theta$: phase rotation angle (degree),
$\gamma$: gyromagnetic ratio (4.258 KHz/Gauss),
$t_p$: application time of gradient magnetic field (msec),
$t_f$: application interval of gradient magnetic field (msec),
$G$: slope of gradient magnetic field (Gauss/cm),
$V$: blood velocity (cm/sec).

In the expression, $t_p$ and $t_f$ defining the flow encode pulse are referred to as scanning parameters and are related as shown in the gradient magnetic field $G_y$ of FIG. 2.

For example, the MR image of a region of interest with phase rotation angle θ of 0° is opposite to that with phase rotation angle θ of 180° in direction of phase rotation of spin. Therefore, images inverted in brightness are formed. If a differential image comprising differences of respective pixels between those two MR images is calculated, therefore, an MR image having the largest intensity value at regions having the same blood velocity as that of the region of interest is obtained. As a result, it is possible to obtain a blood vessel image with a region of interest enhanced.

It is now assumed that the blood velocity at a region of interest is $V_{ROI}$. When the phase rotation angle θ is 0°, it follows that $t_p \cdot t_f = 0$ from the expression (1). It is thus meant that the flow encode pulse is not irradiated. It is understood from the expression (1) that a flow encode pulse satisfying the relation $$t_p \cdot t_f = \frac{\pi}{0.36 \, \gamma \cdot G \cdot V_{ROI}} = a \tag{2}$$

may be used when the phase rotation angle θ is 180°. Therefore, a differential image can be obtained by calculating the difference between an MR image obtained when the flow encode pulse is not applied and an MR image obtained when the flow encode pulse satisfying the expression (2) is applied.

Neglecting the effect of the apparatus distortion and the relaxation time, the signal strength S of each pixel in an MR image obtained by a predetermined scanning sequence is represented as $$S(x,y) = p(x,y) \exp(-i\theta(x,y)) \quad (3)$$

where
(x, y) : position on the screen
S : signal strength
$\rho$: hydrogen atom density
$\theta$: phase rotation angle depending upon the flow velocity.

In this way, the signal strength of each pixel is represented as a product of the density term and the phase term. The density $\rho$ is the absolute value of an NMR signal at each pixel.

By representing $t_p \cdot t_I$ derived from the expression (2) as a and assuming that the phase rotation angle $\theta$ of a region of interest is 180°, the phase rotation angle $\theta$ at an arbitrary position in the MR image is represented as $$\theta = 0.36 \gamma \cdot G \cdot a \cdot V. \quad (4)$$

When the position (x, y) of a region of interest is specified, therefore, a is derived from the flow velocity $V_{ROI}$ at that point on the basis of the expression (2). By substituting this value a and the blood velocity V at each pixel of the MR image derived beforehand into the expression (4), the phase rotation angle $\theta$ of each pixel in the MR image at the time when $\theta$ at the region of interest is 180° is calculated. By substituting the value thus calculated into the expression (3), the signal strength of each pixel in the MR image at the time when $\theta$ at the region of interest is 180° can be derived. From this result, therefore, the MR image at the time when a flow encode pulse is applied can be calculated. The MR image at the time when the pulse is not applied is derived by substituting O into $\theta$ of the expression (3). By calculating and synthesizing a differential image between these two MR images, it is possible to obtain a blood vessel image with an arbitrary region of interest enhanced without performing actual scanning.

Figure 3:
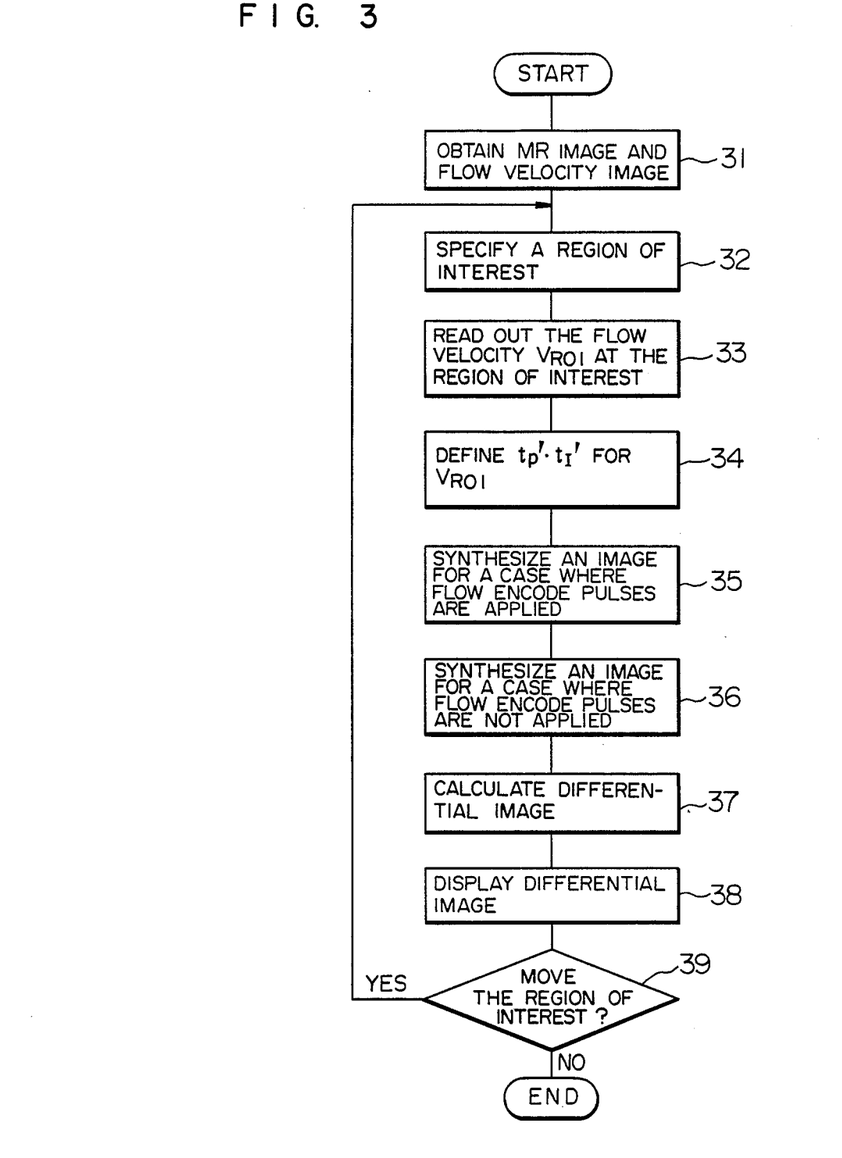
FIG. 3 is a flow chart for explaining the operation of the first embodiment of the present invention.

FIG. 3 is the operation flow chart of the processing unit 16 in a first embodiment of a magnetic resonance image synthesizing system according to the present invention.

In the operation of the present embodiment of the magnetic resonance image synthesizing system, images are scanned by the pulse sequence for measuring the blood velocity, the density and blood velocity at each position on the image are derived (Step 31). Although this operation is explained in the aforementioned U.S. Ser. Nos. 133,069 and 881,505, it will now be described here briefly. A radio-frequency pulse of 90°-180° is applied. In a gradient magnetic field $G_Z$ of the Z-direction, flow encode pulses 23 and 24 are opposite to a flow encode pulse 25 in direction. Further in a gradient magnetic field $G_x$ of the x-direction, flow encode pulses 26 and 27 are opposite to each other in direction. Flow encode pulses 28 and 29 are also opposite to each other in direction. Accordingly, the phase rotation caused by the movement of blood flow into the x-direction is canceled by the phase rotation caused by the movement of blood flow into the Z-direction. Therefore, phase rotation is caused only for the flow velocity of the Y-direction. The phase rotation does not respond to the velocities in the X- and Z-directions.

Accordingly, the phase rotation angle $\theta$ of the measured signal caused by the flow encode pulses 21 and 22 in the gradient magnetic field $G_y$ of the Y-direction is related to the flow velocity $V_y$ as $\theta = 0.36 \gamma \cdot G_y \cdot t_p \cdot t_I \cdot V_y$. Since $\theta$ can be derived from the measured signal and $t_p \cdot t_I$ is defined by the flow encode pulses 21 and 22, it is possible to calculate the flow velocity $V_y$ at each region therefrom and store the distribution of the flow velocity as an image.

On the basis of an operator's command supplied from the manipulation panel 18, a region of interest to be enhanced and displayed is then specified on the screen of the CRT display 17 by a cursor (step 32). The flow velocity at that region is read out from the flow velocity distribution image (step 33). For that flow velocity $V_{ROI}$, $t_p' \cdot t_I'$ is so defined as to satisfy the relation $0.36 \gamma \cdot G \cdot t_p' \cdot t_I' \cdot V_{ROI} = 180°$ (step 34). In this sequence as well, the phase rotation angle of the measured signal responds to only the flow velocity in the Y-direction.

By referring to $t_p' \cdot t_I'$ thus defined as well as density and flow velocity information at each position on the image enhanced beforehand and by using the expressions (3) and (4), images are then synthesized for a case where flow encode pulses 41 and 42 are applied and a case where these pulses are not applied as shown in FIG. 4 (steps 35 and 36).

Succeedingly, subtraction is performed between the two synthesized images calculated as described above (step 37), and the resultant differential image is displayed on the CRT display 17 (step 38). This calculation is performed by taking a pixel as unit. For a region like a background where the absolute value of the signal is very small or a region which has a low velocity and which is determined to be stationary, it is not necessary to perform this calculation. In that case, the density values on the density image scanned beforehand are adopted as values on the synthesized image.

If it is directed to change the region of interest to be enhanced by the manipulation panel 18 (step 39), $t_p' \cdot t_I'$ is defined from the blood velocity of the region of interest and the processing heretofore described is repeated (steps 32 to 34).

If the region of interest to be enhanced is not changed (step 39), the processing is finished.

Synthesis of an image with the relaxation time enhanced which is a second embodiment of the present invention will now be described.

In this embodiment, a one-dimensional or two-dimensional scanning parameter specifying area is provided on the screen of the display 17. Computation is performed by using values of parameters specified by moving the position of the cursor and using the information of relaxation time and information of nuclide density obtained from a plurality of images with relaxation time enhanced which were scanned beforehand. A synthesized image is thus calculated and displayed. Or a region of interest is specified by moving a cursor on a displayed image. The relaxation time of the region of interest is calculated from a plurality of images with relaxation time enhanced which were scanned beforehand. On the basis of the calculated value, scanning parameters are so defined as to maximize the image contrast of the region of interest. A synthetic image is calculated and displayed by using the above described method.

In this case, a generally known method as described in the aforementioned "Clinical Evaluation of Synthetic MR images in Intracranial Diseases" is adopted as the method for calculating an image with relaxation time enhanced under the condition that respective scanning parameters are arbitrarily changed.

For example, observed signals S1, S2 and S3 at an arbitrary point respectively obtained by using pulse sequences (a) and (b) of the spin echo method and a pulse sequence (c) of the inversion recovery method are approximated as $$S_1 = \rho \exp(-TE_1/T_2) \quad (5)$$

$$S_2 = \rho \exp(-TE_2/T_2) \quad (6)$$

$$S_3 = \rho\{1 - 2\exp(-TI_1/T_1)\} \cdot \exp(-TE_1/T_2) \quad (7)$$

where
$\rho$: spin density
$T_1$: spin-lattice relaxation time
$T_2$: spin-spin relaxation time.

Figure 5:
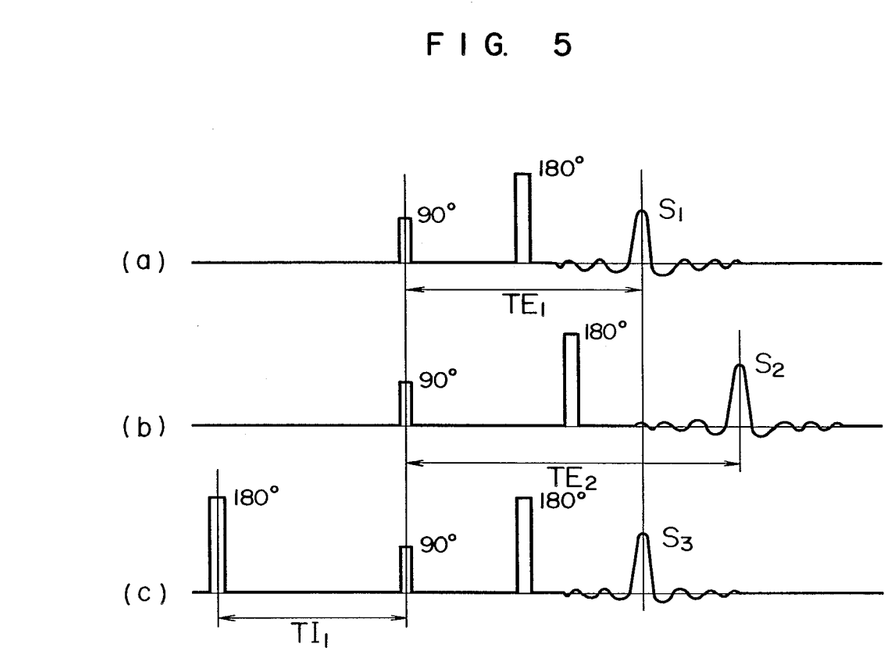
FIG. 5 shows a pulse sequence for scanning a plurality of MR images in the second embodiment of the present invention.

In these expressions, $TE_1$, $TE_2$ and $TI_1$ are values of scanning parameters as illustrated in FIG. 5 and are arbitrarily set from the outside. Therefore, values of $\rho$, $T_1$ and $T_2$ are derived from simultaneous equations (5) to (7). In this case, the observed signal S at each point of the inverted and rotated image at the time when arbitrary scanning parameters Ti and TE are set is represented as $$S = \rho\{1 - 2\exp(-TI/T_1)\} \cdot \exp(-TE/T_2). \quad (8)$$

If $\rho$, $T_1$ and $T_2$ are already known, therefore, the observed signal S can be calculated.

Otherwise, the expression (8) is transformed by using the expressions (5) to (7) as $$S = S_1\{1 - 2((S_1-S_3)/2S_1)^{TI/TI_1}\} \times (S_1-S_2)^{TE/-TE^1)/(TE^1 - TE^2)}. \quad (9)$$

Accordingly, S can be calculated when TI and TE are arbitrarily set. Therefore, it is also possible to calculate a synthetic image directly from three images already known.

Figure 6A:
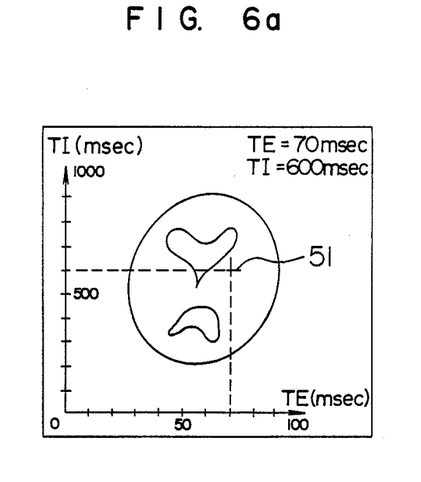
FIGS. 6a and 6b are diagrams for explaining a method of specifying a position on the display screen in the second embodiment of the present invention.

By displaying an image with relaxation time enhanced which is already scanned on the display 17 as shown in FIG. 6a, providing two-dimensional specification areas of TE and TI of the expression (8) or (9), and moving the spin-lattice and spin-spin positions of a cursor 51, therefore, each value of those parameters can be specified by one cursor position. On the basis of the expression (8) or (9), an image with relaxation time enhanced corresponding to the set scanning condition is calculated and displayed. If a doctor thus changes values of TI and TE while continuously moving the cursor, a corresponding MR image is displayed in a moment. Therefore, it is possible to easily track and display the image of inversion recovery having a desired contrast.

Figure 6B:
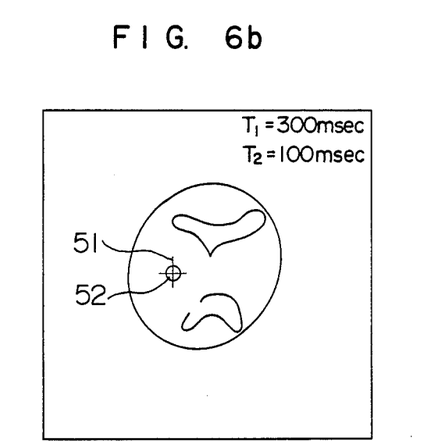

Further, it is also possible to specify an area of interest 52 having a finite size around the cursor 51 as shown in FIG. 6b and maximize the contrast of the image within that area. In this case, the contrast of the image with relaxation time enhanced is maximized by maximizing $X = \delta S/\delta T_1$ and $Y = \delta S/\delta T_2$ in the expression (8). After all, the condition is expressed by $\delta X/\delta TI) = 0$ and $(\delta Y/\delta TE) = 0$, resulting in relations $TI = T_1$ and $TE = T_2$.

By using average values of $T_1$ and $T_2$ in the area of interest as the parameters TI and TE, therefore, an image of inversion recovery maximizing the image contrast within that area is obtained.

An image of saturation recovery can also be synthesized and displayed by a similar method.

Figure 7:
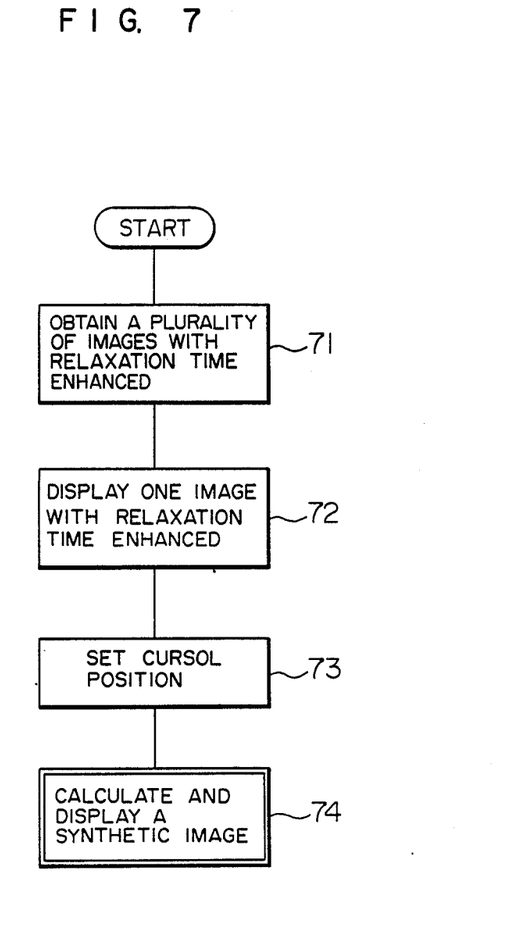
FIG. 7 is a flow chart for explaining the operation of the second embodiment of the present embodiment.

When an image with relaxation time enhanced is to be synthesized in the magnetic resonance image synthesizing system of the present invention, a plurality of images with relaxation time enhanced are first scanned and reconstructed as shown in FIG. 7 (step 71). For example, two spin echo images and one inversion recovery image are scanned by using the spin echo sequences (a) and (b) and the sequence (c) of the inversion recovery method as shown in FIG. 5. In this case, the spin-lattice relaxation time and the spin-spin relaxation time of each pixel are stored in a memory in the form of a table. Succeedingly, one of the enhanced images, such as the inversion recovery image is displayed on the CRT display 17 (step 72).

Succeedingly, the cursor is moved to set a position to be enhanced (step 73). By computation between the scanning condition thus set and information obtained from a Plurality of images already scanned, a synthetic image with relaxation time enhanced is then calculated and displayed (step 74).

Figure 8:
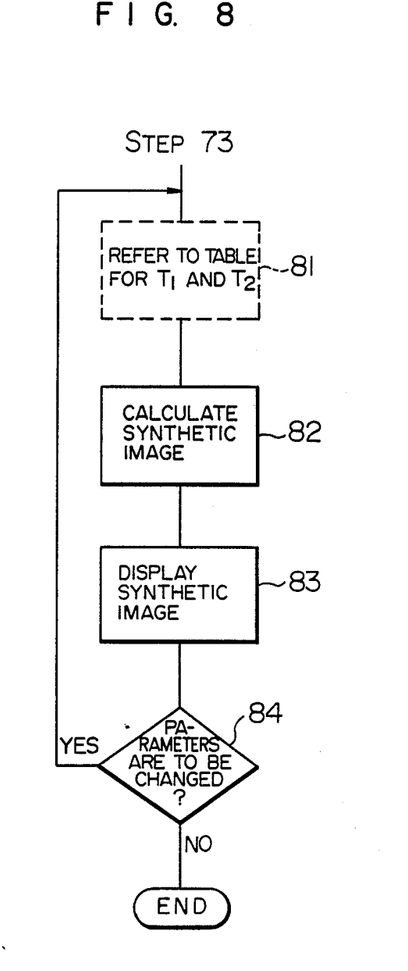
FIGS. 8 and 9 are flow charts showing the operation corresponding to the embodiments shown in FIGS. 6a and 6b.

Since the contents of the Step 74 for calculating and displaying a synthetic image in case of FIG. 6a differ from those in case of FIG. 6b, the step 74 in these cases will now be described by referring to FIGS. 8 and 9, respectively.

In the example wherein the scanning parameters are specified by the cursor as shown in FIG. 6a, an initial inversion recovery image is displayed at step 72, and the manipulation panel 18 is operated at step 73 to set two necessary scanning parameters TE and TI. SucceedinglY at step 81 of FIG. 8, the spin-lattice relaxation time $T_1$ and the spin-spin relaxation time $T_2$ corresponding to each pixel are read out from the table. On the basis of the relaxation time $T_1$ and $T_2$ thus read out and the scanning parameters TE and TI, the observed signal S of each pixel is calculated by using the expression (8) to form a synthetic inversion recovery image at step 82. The synthetic image is displayed on the screen of the CRT display 17 at step 83. If a movement of the cursor is present, it is determined at step 84 that there is a change in the scanning parameters, and the processing returns to the step 81 to repeat the above described operation. If there is no cursor movement, it is determined at step 84 that there is no change in scanning parameters, the flow being finished.

The example using the expression (8) has heretofore been described. In case the expression (9) is used, however, the observed signal of an inversion recovery image is calculated at step 82 from only the scanning parameters TE and TI specified at step 73. Accordingly, the step 81 is omitted.

The case where a region of interest is specified and the contrast at that region is maximized as shown in FIG. 6b will now be described.

Figure 9:
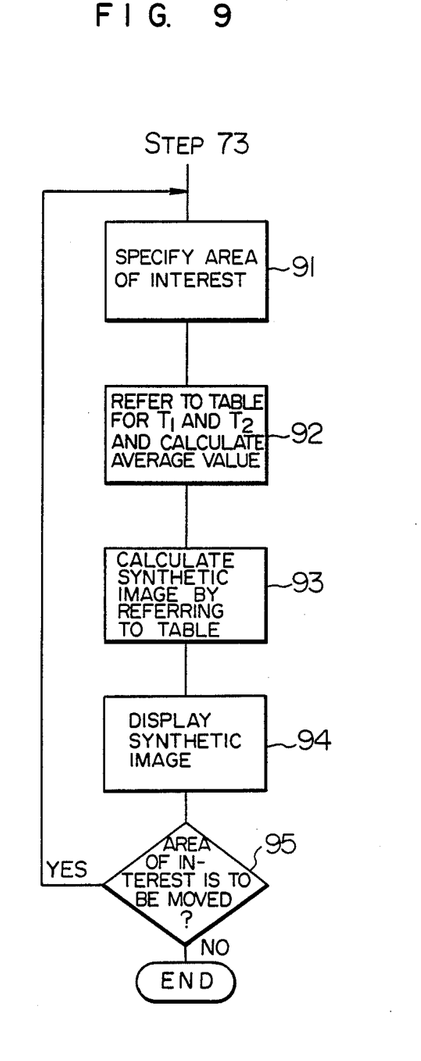

If in this case the cursor is moved to a region of interest on the displayed image at the step 73, a predetermined area around the position specified by the cursor is specified at step 91 of FIG. 9. At step 92, the spin-lattice relaxation time and the spin-spin relaxation time within the area thus specified are read out for each pixel, and the average value of each relaxation time is calculated. Succeedingly at step 93, the average relaxation time values $T_{1a}$ and $T_{2a}$ thus calculated are substituted in the scanning parameters TI and TE of the expression (8). That is to say, under the condition that $TI=T_{1a}$ and $TE=T_{2a}$, the relaxation time table is referred to in accordance with the expression (8). The observed signal of each pixel is thus calculated to derive a synthetic image. And the synthetic image is displayed at step 94. When the cursor is moved, it is determined at step 95 that there is a change in area of interest, and the flow returns to the step 91 to repeat the above described operation. If there is no movement of the cursor, it is determined at step 95 that the area of interest is not to be moved, the flow being finished.

By thus using the known method for calculating a synthetic image and performing the calculation and display of a synthetic image nearly concurrently with movement of the cursor position on the CRT display, images differing in scanning condition or area of interest enhanced can be continuously displayed. As heretofore described, the present invention makes it possible to synthesize an image displaying an arbitrary region of interest on the image at the highest density on the basis of density information and velocity information obtained from an image scanned beforehand without performing actual scanning. As a result, useful diagnostic information can be obtained easily.

In addition, a doctor can set a desired scanning condition in relaxation time enhancement in a form which can be easily grasped visually while moving the cursor on the image, and the result is fed back in a moment. By repeating this operation, therefore, a synthetic image with relaxation time enhanced which is the most useful for diagnosis can be easily produced.

We claim:

1. A magnetic resonance image synthesizing system comprising:

means for generating a static magnetic field, a gradient magnetic field and a radio-frequency magnetic field;

means for applying said magnetic fields to an object to be examined having blood flow therein;

means for detecting nuclear magnetic resonance signals supplied from said object to be examined;

sequence control means for controlling the gradient magnetic field and the radio-frequency magnetic field generated by said magnetic field generating means and said detecting means;

means for constructing a magnetic resonance image according to a density distribution of nuclides in which the nuclear magnetic resonance occurs and a velocity distribution of blood flow within said object to be examined on the basis of the nuclear magnetic resonance signals detected by said detecting means;

means for displaying the magnetic resonance image constructed by said construction means;

means for specifying a region of interest in the magnetic resonance image displayed by said displaying means;

means for reading out a blood flow velocity at the region of interest specified by said specifying means from the velocity distribution of blood flow;

means for defining scanning parameters so as to produce a suitable image at a portion having the blood flow velocity read out by said reading means;

synthesizing means for synthesizing a magnetic resonance image on the basis of the scanning parameters defined by said defining means; and means for making said displaying means display the synthesized magnetic resonance image.

2. A magnetic resonance image synthesizing system according to claim 1, wherein said defining means includes means delimiting said scanning parameters so that said portion having said blood flow velocity has the highest intensity.

3. A magnetic resonance image synthesizing system according to claim 2, wherein said defining means defines two kinds of scanning parameters so that measured signals of two magnetic resonance images synthesized by said synthesizing means in accordance with the two kinds of scanning parameters may yield a phase rotation angle difference of 180° at said region of interest, and said synthesizing means includes a first constructing means for constructing a magnetic resonance image with respect to each of said two kinds of scanning parameters and a second constructing means for constructing a differential image between two magnetic resonance images constructed by said first constructing means, and wherein said displaying means displays the differential image calculated by said second constructing means.

4. A magnetic resonance image synthesizing system according to claim 3, wherein said defining means includes means delimiting one of the two kinds of scanning parameters so that a corresponding phase rotation angle is 180°, and said first constructing means constructs one of said two magnetic resonance images for a case where a flow encode pulse is applied and constructs the other of said two magnetic resonance images for a case where said flow encode pulse is not applied.

* * * * *